United States Patent
Coury et al.

[11] Patent Number: 6,162,241
[45] Date of Patent: Dec. 19, 2000

[54] HEMOSTATIC TISSUE SEALANTS

[75] Inventors: Arthur J. Coury, Boston; Amarpreet S. Sawhney, Bedford, both of Mass.; Jeffrey A. Hubbell, Zumikon, Switzerland; C. Michael Philbrook, Boston, Mass.

[73] Assignee: Focal, Inc., Lexington, Mass.

[21] Appl. No.: 09/129,735

[22] Filed: Aug. 5, 1998

Related U.S. Application Data

[60] Provisional application No. 60/054,849, Aug. 6, 1997.

[51] Int. Cl.[7] .................................................. A61B 17/08
[52] U.S. Cl. ............................................. 606/214; 606/213
[58] Field of Search ..................................... 606/213–216; 528/354, 361, 54.1, 54.2; 424/426

[56] References Cited

U.S. PATENT DOCUMENTS

| | | |
|---|---|---|
| 2,642,375 | 6/1953 | Henderson et al. . |
| 3,438,374 | 4/1969 | Falb et al. . |
| 3,483,870 | 12/1969 | Coover et al. . |
| 4,443,430 | 4/1984 | Mattei et al. . |
| 4,511,478 | 4/1985 | Nowinski et al. . |
| 4,532,134 | 7/1985 | Malette et al. . |
| 4,741,872 | 5/1988 | De Luca et al. . |
| 4,826,945 | 5/1989 | Cohn et al. . |
| 4,888,413 | 12/1989 | Domb . |
| 4,938,763 | 7/1990 | Dunn et al. . |
| 5,100,992 | 3/1992 | Cohn et al. . |
| 5,160,745 | 11/1992 | De Luca et al. . |
| 5,304,377 | 4/1994 | Yamada et al. . |
| 5,410,016 | 4/1995 | Hubbell et al. . |
| 5,484,913 | 1/1996 | Stilwell et al. . |
| 5,525,334 | 6/1996 | Ito et al. . |
| 5,525,335 | 6/1996 | Kithara et al. . |
| 5,527,864 | 6/1996 | Suggs et al. . |
| 5,575,995 | 11/1996 | Giovanoni . |
| 5,580,974 | 12/1996 | Banker et al. . |
| 5,583,114 | 12/1996 | Barrows et al. . |
| 5,595,735 | 1/1997 | Saferstein et al. . |
| 5,597,581 | 1/1997 | Kaessmann et al. . |
| 5,641,502 | 6/1997 | Skalla et al. . |
| 5,643,596 | 7/1997 | Pruss et al. . |
| 5,645,849 | 7/1997 | Pruss et al. . |
| 5,658,588 | 8/1997 | Betzinger et al. . |
| 5,690,675 | 11/1997 | Sawyer et al. .......................... 606/229 |
| 5,696,101 | 12/1997 | Wu et al. . |
| 5,714,232 | 2/1998 | Fenton et al. . |

(List continued on next page.)

FOREIGN PATENT DOCUMENTS

| | | |
|---|---|---|
| WO 95/00184 | 1/1995 | WIPO . |
| WO 95/22316 | 2/1995 | WIPO . |

(List continued on next page.)

OTHER PUBLICATIONS

Hemochron "ACT: Activated Clotting Time", Package Insert for ACT Meter Model #801.

Lerner et al. "Current Sstate of Surgical Adhesives", J. Surgical Research, 48:165–181 (1990).

Lupinetti et al., "Cyoprecipitate–topical thrombin glue", J. Thorac. Cardiovasc. Surg. 90:502–505 (1985).

Nakayama et al., "Newly Designed Hemostatic Technology Based on Photocurable Gelatin", ASAIO Journal 1995: 41: M374–378.

Tomizawa et al., "Polyepoxy Compound Cross–Linked Cotton Type Collagen Hemostate", 21st Annual Mtg. Society for Biomaterials, Mar. 18–22 1995, 273.

Nakayama & Matsuda, "Photocurable surgical tissue adhesive glues composed of photoreactive gelatin and poly(ethylene glycol) diacrylate," *J Biomed Mater Res.* 48(4):511–21 (1999).

*Primary Examiner*—Gary Jackson
*Attorney, Agent, or Firm*—Arnall Golden & Gregory, LLP

[57] ABSTRACT

A method of controlling hemostasis by applying a hemostatic agent in a tissue sealant composition. The tissue sealant is a biodegradable, biocompatible synthetic polymer that may not intrinsically possess strong hemostatic properties. Inclusion of a hemostatic material in the tissue sealant can control bleeding at the site and may also provide improved adherence of the sealant to tissue and provide shorter healing times.

18 Claims, 1 Drawing Sheet

U.S. PATENT DOCUMENTS

| | | | |
|---|---|---|---|
| 5,752,974 | 5/1998 | Rhee et al. | 606/214 |
| 5,773,418 | 6/1998 | Edwardson et al. | |
| 5,800,372 | 9/1998 | Bell et al. | |

FOREIGN PATENT DOCUMENTS

| | | |
|---|---|---|
| WO 96/11671 | 4/1996 | WIPO . |
| WO 96/29370 | 9/1996 | WIPO . |
| WO 96/41818 | 12/1996 | WIPO . |

HEMOSTATIC TISSUE SEALANTS

CROSS REFERENCE TO RELATED APPLICATION

Priority is claimed to U.S. provisional application Ser. No. 60/054,849, filed on Aug. 6, 1997.

FIELD OF THE INVENTION

The present invention is in the field of tissue sealants, particularly tissue sealants with hemostatic activity.

BACKGROUND OF THE INVENTION

Tissue sealants are used to decrease or prevent the migration of fluid from or into a tissue. A well known material that has been used as a tissue sealant is "fibrin glue", which is typically made by contacting a solution or suspension of the blood protein fibrinogen with an enzyme or other reagent which will cause fibrin to crosslink. Typically, the enzyme thrombin is used, which cleaves the fibrinogen molecule at specific points to form fibrin monomer, which then spontaneously crosslinks. This is a natural reaction involved in the formation of blood clots. A familiar example of a crosslinked fibrin based material is a scab or an eschar. A disadvantage of fibrin glues is that they have little flexibility or extendibility once their deposition is complete. Moreover, fibrin can be biodegraded in a variable amount of time, depending on a number of uncontrolled parameters, and the duration of a fibrin based tissue sealant is not predictable. Adherence of fibrin clots to tissues can also be unpredictable.

As disclosed in PCT/US96/03834, synthetic materials can be used to make tissue sealants that exhibit high levels of tissue adherence, elastic compliance, and controlled biodegradability. Moreover, these synthetic sealants are completely free of viral and other biological hazards. However, synthetic sealants may not possess significant intrinsic hemostatic properties. Such properties are herein provided by the incorporation of hemostatic materials into one or more of the components of the sealant composition, in advance of or in concurrently with their application to tissue.

SUMMARY OF THE INVENTION

A method of controlling hemostasis by applying a hemostatic agent in a tissue sealant composition is described. The tissue sealant is a biodegradable, biocompatible synthetic polymer that may not intrinsically possess strong hemostatic properties. Inclusion of a hemostatic material in the tissue sealant can control bleeding at the site and may also provide improved adherence of the sealant to tissue and provide shorter healing times.

In a preferred embodiment the tissue sealant is a hydrogel formed from crosslinkable materials having hydrophilic portions and including crosslinkable groups. The hemostatic agent can be incorporated into the crosslinkable material which is applied to the area of tissue where it is desired that hemostasis be prevented. The crosslinkable material is then formed into a hydrogel that seals the tissue.

DETAILED DESCRIPTION OF THE INVENTION

Figure 1:
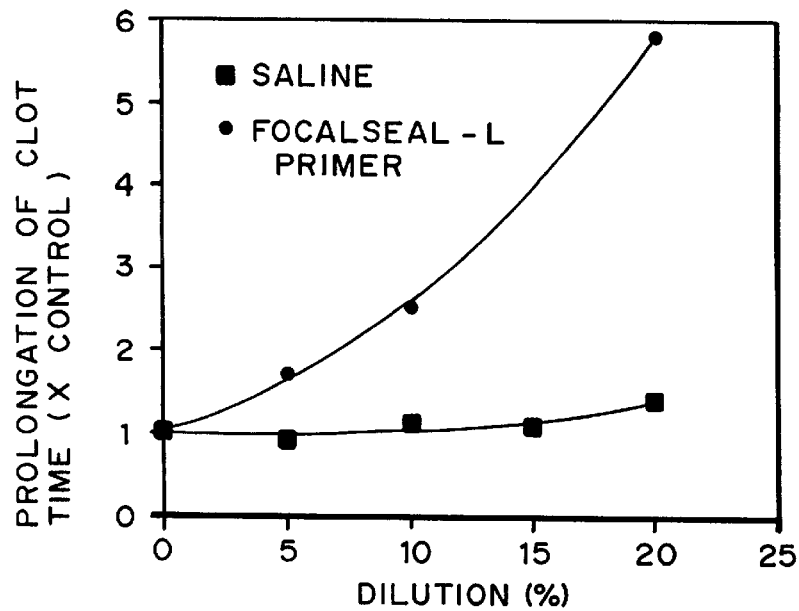
FIG. 1 is a graph that illustrates the effect of dilution of rabbit blood on the time required for the blood to clot. The upper curve represents dilution with a gel forming macromer and the lower curve represents dilution with a saline control.

The materials described herein include crosslinkable molecules suitable for forming a tissue sealant, further incorporating hemostatic materials, also referred to hereinafter as "hemostats". A wide variety of hemostats may be of use, provided that they do not interfere with the formation of crosslinked materials, and are themselves still able to act after exposure to crosslinkable materials. The crosslinked sealant material is biocompatible, biodegradable, and has the ability to seal a tissue or organ against the leakage of bodily fluids, including air.

The crosslinked material is a hydrogel that adheres to tissue in the preferred embodiments. In one preferred embodiment, the hemostat is used in conjunction with a sealant that is applied to a tissue primed with an initiator. The compositions may contain other agents, including additional biologically active materials.

Definitions

A "sealant" is a material which decreases or prevents the migration of fluid from or into a tissue. Sealants are typically applied to a tissue and then locally crosslinked or otherwise processed. The same materials may also be used to adhere structures or tissues together, either when applied between them and crosslinked or processed, or when used to encase junctions of tissue and/or devices.

"Crosslink" is used generically to refer to the joining of smaller entities to form a structure by any physical or chemical means. Unless stated otherwise, the terms "polymerize" and "gel" are functional equivalents of "crosslink".

"Biocompatibility", in the context of the materials and devices of the invention, is the absence of stimulation of a severe, long-lived or escalating biological response to an implant or coating, and is distinguished from a mild inflammation which typically accompanies surgery or implantation of foreign objects into a living organism.

"Biodegradability", in the context of the materials and devices of the invention, is the predictable disintegration of an implant into entities which will be metabolized or excreted, under the conditions normally present in a mammalian organism or living tissue.

"Hemostat" or "hemostatic" refers to a material having the property of stopping the flow of blood, which may include stopping the flow of plasma. A hemostat or hemostatic material may work by any of several mechanisms, as further described.

"Water-soluble" refers to a material soluble to at least 1% by weight in water or an aqueous solution.

Polymeric Compositions

The hemostatic sealants are formed of a crosslinked material, preferably a hydrogel, into which a hemostatic agent is incorporated. The hydrogel is formed of crosslinkable materials (monomers) which contain crosslinkable groups, hydrophilic polymer regions, and preferably, biodegradable regions or linkages. The hydrogels can be formed (crosslinked) prior to application to the tissue or after application to the tissue.

In a preferred embodiment, the hydrogel is formed from biodegradable, polymerizable, macromolecular monomers (macromers) that include a core, an extension on each end of the core, and an end cap on each extension. The core is the hydrophilic polymer or oligomer; each extension is a biodegradable oligomer; and each end cap is an oligomer, dimer or monomer capable of crosslinking the macromers. In a particularly preferred embodiment, the core includes hydrophilic poly(ethylene glycol) oligomers of molecular weight between about 400 and 30,000 Da; each extension includes biodegradable poly (α-hydroxy acid) oligomers of molecular weight between about 200 and 1200 Da; and each end cap includes an acrylate-type monomer or oligomer (i.e., containing carbon-carbon double bonds) of molecular weight between about 50 and 200 Da which are capable of cross-linking and polymerization between copolymers. More specifically, a preferred embodiment incorporates a core consisting of poly(ethylene glycol) oligomers of molecular weight about 10,000 Da; extensions consisting of poly(glycolic acid) oligomers of molecular weight about 250 Da; and end caps consisting acrylate moieties of about 100 Da molecular weight.

Crosslinkable Materials and Groups

U.S. Pat. No. 5,410,016 to Hubbell et al. describes the application of biodegradable macromers to tissue, followed by photopolymerization to form a gel. In addition to the photopolymerizable gels described by Hubbell et al., gels are described in U.S. Pat. No. 4,938,763 to Dunn et al., U.S. Pat. Nos. 5,100,992 and 4,826,945 to Cohn et al., U.S. Pat. Nos. 4,741,872 and 5,160,745 to De Luca et al., U.S. Pat. No. 5,527,864 to Suggs et al., U.S. Pat. No. 4,511,478 to Nowinski et al., and U.S. Pat. No. 4,888,413 to Domb. The materials described in these publications, which covalently crosslink by free radical initiated polymerization, are the preferred materials for use as described herein. However, materials which crosslink by other mechanisms, such as by the reaction of polyisocyanates with polyamines, or which comprise low-molecular weight reactive monomers, may also be suitable if they are biocompatible and non-toxic. The macro monomers ("macromers") which are crosslinkable to form hydrogels may comprise a block copolymer. The macromers can be quickly crosslinked from aqueous solutions. The macromers may advantageously be capable of crosslinking by thermoreversible gelation, and may be crosslinked from a solution state, from a gel state, or from a solid state.

The monomers or macromers preferably include crosslinkable groups which are capable of forming covalent bonds while in aqueous solution. These crosslinkable groups permit crosslinking of the macromers to form a gel. The macromers may also gel by thermally reversible interactions or by ionic interactions, as a primary gelling mechanism or in addition to a covalent crosslinkage. All such methods of gel formation are referred to as "crosslinking" herein, unless specified more narrowly. Chemically or ionically crosslinkable groups known in the art may be provided in the macromers to provide crosslinking potential. The crosslinkable groups in one preferred embodiment are polymerizable by photoinitiation by free radical generation, most preferably by visible or long wavelength ultraviolet radiation. The preferred crosslinkable groups are unsaturated groups, especially hydrocarbon unsaturated groups, including without limitation vinyl groups, allyl groups, cinnamates, acrylates, diacrylates, oligoacrylates, methacrylates, dimethacrylates, oligomethacrylates, methacrylamides, acrylic esters including hydroxyethylmethacrylates, and other biologically acceptable photopolymerizable groups. These groups can also be crosslinked by chemical or thermal means, or by any combination of chemical, thermal and photointiation means.

Other crosslinking chemistries which may be used include, for example, reaction of amines or alcohols with isocyanate or isothiocyanate, or of amines or thiols with aldehydes, epoxides, oxiranes, or cyclic imines. Either the amine or thiol, or the other reactant, or both, may be covalently attached to a macromer. Copolymers from mixtures of monomers are also contemplated. Sulfonic acid or carboxylic acid groups may also be contained in the monomers.

Preferably, at least a portion of the macromers will be crosslinkers, i.e. will have more than one crosslinkable reactive group, to permit formation of a coherent hydrogel by ensuring the crosslinking of the polymerized macromers. Up to 100% of the macromers may have more than one reactive group. Typically, in a synthesis, the percentage will be on the order of 50% to 95%, for example, 60% to 80%. The percentage may be reduced by addition of co-monomers containing only one active group. A lower limit for crosslinker concentration will depend on the properties of the particular macromer and the total macromer concentration, but will be at least about 2% of the total molar concentration of reactive groups. More preferably, the crosslinker concentration will be at least 10%, with higher concentrations, such as 30% to 90%, being optimal for maximum retardation of diffusion of many drugs. Optionally, at least part of the crosslinking function may be provided by a low-molecular weight crosslinker.

When the reactive group is a reactive group which reacts with only one other group, for example, an isocyanate, then at least some, for example at least about 1%, preferably 2% or more, more typically 5% or more, and optionally up to 100%, of the reactive molecules must contain three or more reactive groups to provide crosslinking. In some chemistries, such as epoxides reacting with primary amines, one group will be mono-reactive (in this example, epoxide) and the other will be multifunctional (in this case, amine, which can react with at least two epoxides). In such a reaction, there are several ways in which the required amount of crosslinking can be supplied, with a minimum requirement of some tri-epoxide or some dimeric primary amine.

When the hemostatic agent or other biologically active agent to be delivered is a macromolecule, higher ranges of polyfunctional macromers, i.e. having more than one reactive group, are preferred. If the gel is to be biodegradable, as is preferred in most applications, then the crosslinking reactive groups in the molecule should be separated from each other by biodegradable links. Any linkage known to be biodegradable under in vivo conditions may be suitable, such as a degradable polymer block. The use of hydrocarbon unsaturated groups, crosslinked by free radical polymerization with chemical and/or photoactive initiators, is preferred as the crosslinkable group.

The macromer may also include an ionically charged moiety covalently attached to a macromer, which optionally permits gelation or ionic crosslinking of the macromer.

Hydrophilic Regions

Water soluble hydrophilic oligomers available in the art may be incorporated into the biodegradable macromers. The hydrophilic region can be, for example, polymer blocks of poly(ethylene glycol) (or the synonymous poly(ethylene oxide) or polyoxyethylene), poly(propylene glycol), poly(vinyl alcohol), poly(vinylpyrrolidone), poly(ethyloxazoline), or polysaccharides or carbohydrates including hyaluronic acid, dextran, heparin sulfate, chondroitin sulfate, heparin, alginate, polypeptides including gelatin, collagen, albumin, ovalbumin, and synthetic polyamino acids.

Biodegradable Regions

Biodegradable linkages or polymer or copolymer segments from molecules available in the art may be incorporated into the macromers. The biodegradable region is preferably hydrolyzable under in vivo conditions. In some embodiments, different properties, such as biodegradability and hydrophobicity or hydrophilicity, may be present within the same region of the macromer.

Useful hydrolyzable groups include polymers and oligomers of glycolide, lactide, epsilon caprolactone, and other hydroxy acids, and other biologically degradable polymers that yield materials that are non-toxic or present as normal metabolites in the body. Preferred poly(alphahydroxy acids) are poly(glycolic acid), poly(DL-lactic acid) and poly(L-lactic acid). Other useful materials include polyamino acids, polycarbonates (especially alkyl polycarbonates including poly (trimethylene carbonate)), polydioxanones, poly (anhydrides), poly(orthoesters), poly(phosphazines) and poly(phosphoesters). Polylactones such as poly(epsilon-caprolactone), poly(delta-caprolactone), poly(delta-valerolactone) and poly(gamma-butyrolactone), for example, are also useful. Mixtures of these degradable linking groups may be used. The biodegradable regions may have a degree of polymerization ranging from one up to values that yield a product that is not substantially water soluble. Thus, monomeric, dimeric, trimeric, oligomeric, and polymeric regions may be contained in the macromers.

Biodegradable regions can be constructed from polymers or monomers using linkages susceptible to biodegradation, such as ester, amide, peptide, carbonate, urea, anhydride, orthoester, phosphazine and phosphoester bonds. The time required for a polymer to degrade can be tailored by selecting appropriate monomers. Differences in crystallinity also alter degradation rates. For relatively crystalline or hydrophobic polymers, actual mass loss may occur by fragmentation or may begin when the oligomeric fragments are small enough to be water soluble. Thus, initial polymer molecular weight and structure will influence the degradation rate.

Photoinitiators and/or Catalysts

Useful photoinitiators are those which can be used to initiate by free radical generation polymerization of the macromers without cytotoxicity and within a short time frame, minutes at most and most preferably seconds. Preferred dyes as initiators of choice for LWUV initiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin and triethanolamine, for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example.

Initiation of polymerization can be accomplished by irradiation with light at a wavelength of between about 200–700 nm, most preferably in the long wavelength ultraviolet range or visible range, 320 nm or higher, most preferably about 514 nm or 365 nm.

Elastic and other physical properties

Preferred materials have suitable elastic and stiffness properties which allow them to maintain a sealing function on the tissue to which they are applied. The hemostat containing materials of the invention are not required to have particular elastic properties except as required to serve their function as sealants in a particular application. Mechanical properties are measured by appropriate means, as described in textbooks.

Hemostatic Agents

The materials listed below are known as hemostatic agents in therapeutic practice. To make the tissue sealant hydrogel more hemostatic, the hemostat is incorporated into the hydrogels. The hemostatic agents can be combined into either homophase or heterophase mixtures. The agents may be simply mixed into a solution of the crosslinkable hydrogels, whereupon they will be physically retained by the hydrogel upon its formation. Alternatively, the hemostatic agents may be incorporated as covalent or ionic conjugates, incorporated in the form of microspheres, incorporated by covalent attachment to molecules for sustained release or improved incorporation (as, for example, by reaction with hydroxy-acid conjugates of polyethylene glycol), or by other means.

The hemostatic agents may operate independently of or in conjunction with processes used to apply and form hydrogels. For example, iron salts, which make effective hemostats, may serve the added purpose of participating in the initiation of crosslinking.

The hemostatic performance of hydrogels may achieve high levels by the combined use of effective priming and instant or very fast formation of hydrogel solids of relatively high strength. Subsequent induction of crosslinking may or may not be needed. Additional effectiveness of the hydrogel as a hemostat may stem from its ability to absorb and immobilize blood, or from its formation of adherent barrier at the surface of the tissue to prevent flowing or oozing of fluids from the tissue.

In addition to the hemostats listed below, other materials, such as quaternary ammonium compounds, amines or polyamines, acting separately or as conjugates to the hydrogels, may act to provide effective hemostasis. Combinations of the materials listed, with or without the additional of other active materials, are possible.

Hemostatic agents may be any of several classes of compound. Where the hemostatic materials are proteins or other polypeptides, the hemostatic agents may be derived from natural materials, or be materials produced by recombinant DNA technology, or mutants of natural proteins, or produced by chemical modification of proteins. Combinations of hemostats are contemplated in the invention. The classes of hemostatic agents listed below, and the particular exemplars of each class, are to be construed as exemplary rather than limiting.

Hemostats may, for example, be members of the natural coagulation pathway ("coagulation factors"). Such proteins include, among others, tissue factors, factors VII, VIII, IX, and XIII, fibrin, and fibrinogen.

Hemostatic agents may also be proteins or other compounds which activate or catalyze the natural pathways of clotting ("coagulation activators"). These include thrombin, thromboplastin, calcium (e.g. calcium glucuronate), bismuth compounds (e.g. bismuth subgallate), collagen, desmopressin and analogs, denatured collagen (gelatin), and fibronectin. Vitamin K may contribute to activation of coagulation.

Hemostats may act by activating, aggregating or stimulating platelets ("platelet activators"). These include cycloheximide, N-monomethyl L-arginine, atrial naturetic factor (ANF), small nucleotides (including cAMP, cGMP, and ADP), prostaglandins, thromboxanes and analogs thereof (such as U4-6619 by Upjohn), platelet activating factor, phorbols and phorbol esters, ethamsylate, and hemoglobin. Nonabsorbable powders such as talc, and denatured or surface-absorbed proteins can also activate platelets.

Hemostats may act by local vasoconstriction ("vasoconstrictors"). Examples include epinephrine (adrenaline), adrenochrome, tetrahydrozoline, antihistamines (including antazoline), oxymetazoline, vasopressin and analogs thereof, and cocaine.

Hemostats may act by preventing destruction or inactivation of clotting reactions ("fibrinolysis inhibitors"). Examples include eosinophil major basic protein, aminocaproic acid, tranexamic acid, aprotinin (Trasylol™), plasminogen activator inhibitor, plasmin inhibitor, alpha-2-macroglobulin, and adrenoreceptor blockers.

Hemostats may strengthen clots when formed ("crosslinkers"). Examples include entactin, transglutaminases, and chemical crosslinking agents.

Hemostats may comprise non-protein polymers which act to locally viscosify or gel blood or plasma, by interaction with proteins, by tamponnade, or by other mechanisms ("polymeric hemostats"). Examples include oxidized cellulose, "Vicryl" and other polyhydroxyacids, microfibrillar collagen, crosslinked collagen, collagen sponges, chitosan, alginate, polyacrylic acids, pentosan polysulfate, carrageenan, and polyorthoesters (e.g. Alzamer™).

Hemostats may be materials which form a barrier to blood leakage by mechanical means not directly related to the natural clotting mechanisms ("barrier formers"). These include collagen, denatured collagen, oxidized cellulose, ionically or hydrogen-bond crosslinked natural and synthetic polymers including chitin, chitosan, alginate, pectin, carboxymethylcellulose, and poloxamers such as Pluronic™ surfactants.

In patients who are anti-coagulated, agents which reverse or act as an antidote to the anticoagulation are useful as hemostats ("coagulation restorers"). These include protamine and heparinase.

Among these, preferred materials include epinephrine, adrenochrome, collagen and derivatives, thrombin, fibrin, fibrinogen, oxidized cellulose and chitosan.

An effective amount of a hemostatic agent, for the purposes of this invention, is an amount which is sufficient to stop bleeding from a surface of the type intended for treatment within a medically-acceptable time. In the context of closing after a surgical procedure, a time of 20 minutes or less is acceptable; shorter times are preferred, including 10 minutes or less, 5 minutes or less, 2 minutes or less, and most preferably less than 1 minute.

The ultimate test of the appropriate concentration of hemostats will be determined in vivo. In vitro tests may also be used, such as those reported in the medical literature, to determine the approximate range of concentration. An in vitro test might comprise, for example, determining the time to induce clotting of a drop of fresh blood by a test sample of prepared hemostat containing sealant gel, as illustrated below in Example 1. A suitable in vivo test would be the time to achieve hemostasis on application of a hemostat containing sealant composition to a standard wound, such as a standard full thickness dermal punch on the shaved back of an anesthetized rat. Times to stop blood flow from other surgical wounds, such as wounds of the spleen, liver, blood vessels, etc. can also be suitable. By application of such procedures, the suitability and appropriate concentration of a hemostatic agent may be determined without undue experimentation.

Methods for making the compositions

Methods for making the crosslinking materials are disclosed in the prior art references. For example, methods of making macromers having of a core of poly(ethylene glycol); extensions of poly(glycolic acid); and end caps of acrylate moieties are disclosed in U.S. Pat. No. 5,410,016.

The hemostatic agent can be physically or chemically combined with the crosslinking materials. In a preferred embodiment, the crosslinkable materials will be in solution and the hemostatic agent can be mixed into the solution.

Methods for using the compositions

The hemostatic sealants can be applied in any convenient manner which is effective. The manner of application will depend upon the properties of the sealant that is used. In a preferred embodiment, the hemostatic agent is mixed into the sealant composition, or into one component of it, and the sealant materials are applied in the usual fashion for such sealant. The sealant may be a liquid, or may be partially or completely pre-formed into a tissue coating before application.

Application of a fluid sealant, with or without hemostat, may be made by any conventional means. These include dripping, brushing, or other direct manipulation of a fluid on the tissue surface, and spraying of the fluid sealant onto the surface. Semisolid materials may be delivered by such means if further crosslinking is to occur at the surface. Solid materials are applied by conventional means appropriate to the type of tissue and the surgical procedure. If the surgery is open, application by hand or forceps or the like is contemplated. In endoscopic surgery, material is delivered through the cannula of a trocar, and is spread at the site by any of the various devices known in the art. Alternatively, the hemostatic agent may be applied directly to the tissue, and then the sealant material may be applied on top of the hemostat. If the sealant is partially or fully preformed, then the hemostat may be applied to the sealant, and the composite material is then applied to the tissue as described above.

In one embodiment, one or more initiators or components of an initiation system are applied directly to the surface as a primer, and the unabsorbed excess is optionally removed by washing or blotting. The initiator solution may further contain one or more polymerizable monomers, and other useful formulating ingredients, including accelerators, co-initiators, sensitizers, and co-monomers. Then a liquid containing crosslinkable macromers in combination with one or more initiators or components of an initiation system, which may be the same as or different from that absorbed in the first step, is applied. The system, if not self-polymerizing, is then stimulated to polymerize, for example by application of an appropriate wavelength of light.

The priming and macromer-application steps can also be combined. For example, if excess initiator is not removed before monomer addition, then subsequent application of macromer will result in mixture of initiator into the monomer layer. Similarly, if the macromer layer contains an initiator with a high affinity for the surface, then it is possible to apply a macromer layer containing initiator, and wait an appropriate time to allow preferential absorption of the initiator to the surface, to achieve the same effect.

The present invention is further described by the following non-limiting examples.

EXAMPLE 1

Demonstration of Hemostasis with Combination of Sealant and Hemostatic Agent

The interaction among rabbit blood, hemostatic materials, and a gel-forming macromer was determined. The interactions were determined by measurement of the Accelerated Clotting Time (ACT), a standard and well known clinical test. In this test, a standard amount of a clotting accelerator, such as diatomaceous earth (DE), is placed in a test tube, and the time required for blood to clot in its presence is measured. ACT was determined with a standardized commercial system (Hemochron ACT Meter Model 801 and tubes FTCA510; from International Technidyne Corp., Edison N.J.).

In a first set of experiments, shown in FIG. 1, freshly drawn rabbit blood was mixed with either normal saline or with a photopolymerizable macromer material. The macromer contained a polyethylene glycol core, with short polylactic acids blocks on each end, terminated with acrylate groups. It was added in the form of an aqueous solution containing salts, buffers, and other excipients, in a form suitable for use in humans. It was found that dilution of the blood with saline did not significantly alter the clotting time, while dilution with the macromer solution retarded clotting, implying an inherent anticoagulant effect of the material.

Figure 2:
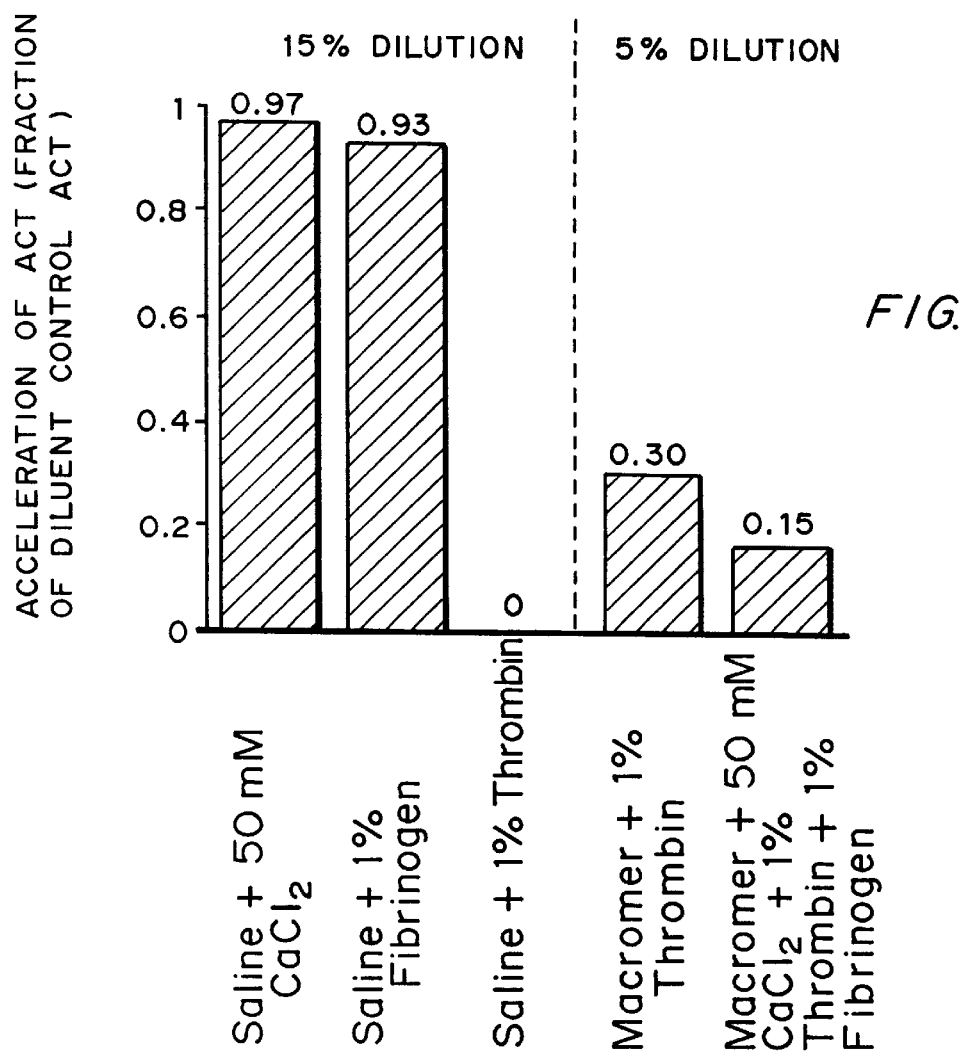
FIG. 2 is a bar graph that illustrates the effects of addition of various agents on the clotting time of blood diluted with saline and blood diluted with a gel forming agent.

In a second set of experiments, the results of which are shown in FIG. 2, the effect of known hemostatic agents on the clotting time of rabbit blood diluted with saline (control) or with macromer solution was determined, as measured by the ACT test. The same macromer was used. The three bars to the left are controls. In the saline controls, it was found that 1% thrombin greatly accelerated the rate of clotting in the ACT, although fibrinogen alone or calcium alone had no significant effect. It was found that thrombin also greatly accelerated the rate of clotting in the macromer containing blood, while further addition of calcium and fibrinogen further accelerated clotting.

Although the hydrogel sealant material on its own inhibited clotting, as compared to the control, it allowed clotting when combined with the hemostatic agents thrombin, calcium, and fibrinogen. The utility of the sealant/hemostat is its ability to act as a sealant, which assists in retarding blood flow on its own, combined with its ability to provide hemostasis at the site of injury. Moreover, the sealant ability of the hydrogel should be improved because accelerated clotting of bleeding from a surface to be treated should improve the adherence of the sealant to the tissue surface.

Modifications and variations of the present invention will be obvious to those skilled in the art from the foregoing detailed description and are intended to be encompassed by the following claims.

We claim:

1. A hemostatic tissue sealant, comprising:
a biocompatible, biodegradable hydrogel tissue sealant comprising crosslinkable groups having incorporated therein an effective amount of a hemostatic agent to stop the flow of blood from tissue in a medically acceptable period of time.

2. A hemostatic tissue sealant as in claim 1, wherein the hemostatic agent is selected from the group consisting of coagulation factors, coagulation initiators, platelet activators, vasoconstrictors, and fibrinolysis inhibitors.

3. A hemostatic tissue sealant as in claim 1, wherein the hemostatic agent is selected from the group consisting of epinephrine, adrenochrome, collagens, thrombin, fibrin, fibrinogen, oxidized cellulose, and chitosan.

4. A hemostatic tissue sealant as in claim 1, wherein the crosslinkable materials are self-crosslinking to form a seal.

5. A hemostatic tissue sealant as in claim 1, wherein the hydrogel is a photopolymerizable gel.

6. A hemostatic tissue sealant as in claim 1, wherein the hydrogel tissue sealant is formed of crosslinkable materials which contain crosslinkable groups, hydrophilic regions, and biodegradable regions.

7. A hemostatic tissue sealant as in claim 6, wherein the crosslinkable materials covalently crosslink by free radical initiated polymerization.

8. A hemostatic tissue sealant as in claim 6, wherein the crosslinkable materials are crosslinked by the application of one or more initiators of polymerization.

9. A hemostatic tissue sealant as in claim 8, wherein the one or more initiators of polymerization comprise oxidizers, heat and light.

10. A hemostatic tissue sealant as in claim 6, wherein the crosslinkable materials covalently crosslink by free radical initiated polymerization.

11. A hemostatic tissue sealant as in claim 6, wherein the hydrophilic regions comprise polyethylene glycol, the crosslinkable groups comprise hydrocarbon unsaturated groups and the biodegradable regions comprise poly (hydroxy acid).

12. A hemostatic tissue sealant composition comprising a biodegradable, biocompatible crosslinkable material that will function as a tissue sealant when crosslinked, having incorporated therein a hemostatic agent in an amount sufficient to stop the flow of blood from a tissue surface in a medically acceptable amount of time.

13. A method for forming a hemostatic sealant on a tissue surface, comprising:
applying the hemostatic sealant composition of claim 12 to the tissue surface; and
crosslinking the crosslinkable groups.

14. The method of claim 13, wherein the crosslinkable material includes crosslinkable groups, hydrophilic regions, and biodegradable regions.

15. The composition of claim 12, wherein the hydrophilic regions comprise polyethylene glycol, the crosslinkable groups comprise hydrocarbon unsaturated groups and the biodegradable regions comprise poly(hydroxy acid).

16. The method of claim 13, further comprising the step of applying an initiator primer to the tissue surface prior to application of the hemostatic sealant composition.

17. The composition of claim 12, wherein the hemostatic agent is selected from the group consisting of coagulation factors, coagulation initiators, platelet activators, vasoconstrictors, and fibrinolysis inhibitors.

18. The composition of claim 12, wherein the hemostatic agent is selected from the group consisting of epinephrine, adrenochrome, collagens, thrombin, fibrin, fibrinogen, oxidized cellulose, and chitosan.

* * * * *